United States Patent [19]
Musow et al.

[11] Patent Number: 5,106,478
[45] Date of Patent: Apr. 21, 1992

[54] ELECTRODE WIPER CLEANING SYSTEM

[76] Inventors: Wolf Musow, 18 White Oak Dr., Plymouth, Mass. 02360; Norman D. Gilmartin, 55 Third Ave., Osterville, Mass. 02655; Steve Pedro, 11 Bunnys Rd., Plymouth, Mass. 02360; Louis St. Onge, 3615 Rue du Park, CP 842, Mont Rolland, P.Q., Canada, J)R 1G0

[21] Appl. No.: 623,635

[22] Filed: Dec. 6, 1990

[51] Int. Cl.5 .............................................. G01N 27/26
[52] U.S. Cl. .................................................... 204/402
[58] Field of Search .................. 204/402, 279, 297 R; 324/79, 32, 33

[56] References Cited
U.S. PATENT DOCUMENTS

| 4,021,199 | 5/1977 | Mukae et al. | 204/402 |
| 4,668,369 | 5/1987 | King | 204/279 |

Primary Examiner—John Niebling
Assistant Examiner—Bruce F. Bell
Attorney, Agent, or Firm—Jules Jay Morris

[57] ABSTRACT

An improved electrode cleaning system for an electrochemical sensor is disclosed. The improved electrode cleaning system includes a flexible wiper blade which is biased against a flat wiping surface formed by electrodes having a flat detection surface and a collar placed around the electrodes to prevent particulates from depositing between the electrodes. The collar is secured to the sensor by a recessed screw which also serves as a common electrical ground. The flexible blade preferably has two wiping portions for alternately wiping the electrodes and the common ground screw.

17 Claims, 3 Drawing Sheets

ELECTRODE WIPER CLEANING SYSTEM

FIELD OF THE INVENTION

The present invention relates to an improved electrode cleaning system for an electrochemical sensor.

BACKGROUND OF THE INVENTION

Electrochemical sensors, such as The Foxboro Company's 871PH Sensor, include a glass or metal sensing electrode and a reference electrode which are immersed into a process solution to measure the solution's pH (acidity) or ORP (oxidation reduction potential). Typically, a post extends from the sensor into the process solution and serves as a common electrical ground. The sensing electrode produces an electrical potential proportional to the hydrogen ion activity (for pH sensors) or oxidation activity (for ORP sensors). The reference electrode completes the circuit and provides a stable reference for the sensing electrode. These two electrodes constitute an electrolytic cell having a continuous millivolt output that is proportional to the pH or ORP of the solution.

Continuous on-line pH or ORP measurements are very important for many liquid processes. For example, in the manufacture of fine and specialty paper, tight control over the pH value of the pulp is necessary to ensure total paper quality. Typical ORP applications include treatment of chromate and cyanide wastes produced by plating, chemical, and metal treatment plants. ORP monitoring enables industry to determine reaction end points to meet today's stringent environmental requirements. A problem often encountered with these sensors, however, is that particulates in the process solution, for example the pigments, fillers, and dyes used in the manufacture of paper, bond to the sensor surfaces. Over time the electrodes and the common ground become coated and the measurements may become unreliable. To avoid removing the sensor for external cleaning of the electrodes and the common ground and to provide continuous, accurate pH and ORP sensing, two entirely different electrode cleaning systems were developed: an ultrasonic cleaning system and a mechanical cleaning system.

The ultrasonic cleaner consists of a disk-shaped transducer positioned very close to the sensing and reference electrodes. Ultrasonic energy waves are generated to keep particulates in suspension and prevent them from settling on any surface within reach of the ultrasonic waves. Tests have demonstrated, however, that very fine particles do settle on and eventually coat the electrode and common ground surfaces. This necessitates continued periodic removal of the electrodes for external cleaning.

Mechanically cleaning the electrodes is an entirely different approach. This approach typically includes a rotating brush which continuously sweeps clean the surface detection areas of both electrodes. The electrodes used in this cleaning system have flat detection surfaces. Over time, however, these brushes accumulate filler material, pigments and other matter which prevent the brushes from properly cleaning the electrodes.

Electrode sensitivity problems were also encountered with these cleaning systems when large amounts of stock accumulated around and between the electrodes. To prevent this accumulation and to minimize the down time required for external cleaning of the electrodes, the sensor is commonly placed on a sample line connected to the main stream of process solution. Periodically, the sample line is isolated from the main line and flushed to dislodge and remove all of the accumulated stock and filler away from the electrodes and cleaner brush. After flushing, the sample line is again connected to the main stream of process solution. During this time, however, measurements of the process fluid are lost.

SUMMARY OF THE INVENTION

It is therefore an object of the present invention to provide an improved cleaning system for an electrochemical sensor which cleans the electrodes of the sensor and allows it to provide uninterrupted, continuous measurements of the process solution.

It is another object of the present invention to provide an improved cleaning system for an electrochemical sensor that does not require the electrodes to be periodically removed and externally cleaned.

It is another object of the present invention to provide an improved cleaning system for an electrochemical sensor that does not require the electrodes to be periodically flushed with cleaning fluid.

It is yet another object of the present invention to provide an improved electrode cleaning system which prevents particulates of a process solution from accumulating on or around the electrodes of the electrochemical sensor.

It is yet another object of the present invention to provide an improved electrode cleaning system that evenly secures and holds the sensing electrodes in place as they are scraped clean.

It is a further object of the present invention to remove the build-up of particulates of the process solution on a common electrical ground of the sensor.

The present invention results from the realization that an improved electrode cleaning system could be manufactured by providing a collar around the electrodes, having a flat detection surface, to prevent accumulation of particulates of a process solution from collecting around the electrodes. The collar should be manufactured to securely fit about the electrodes to evenly secure and hold them in place when they are cleaned. It was further realized that the collar should also include a flat wiping surface that is flush with the flat detection surfaces of the electrodes and be anchored to the sensor by a recessed screw which could serve as a common electrical ground. The build-up of particulates can then be removed by providing a flexible rotating wiper blade which is biased against and scrapes clean the wiping surface areas of the electrodes, the ground screw and the collar. A wiper blade having flat, smooth surface areas would prevent particulates from building up on the blade as it rotates in a process stream.

The electrode cleaning system of the present invention includes a flexible wiper blade which is rotated about its axis to scrape clean electrodes of an electrochemical sensor. The wiper blade has smooth surfaces, which together with its movement and the stream velocity of the process fluid, prevent particulates from accumulating on its surfaces. A spring mechanism is used to push the flexible wiper blade towards the surfaces of the electrodes to scrape the wiping surfaces of the electrodes clean. A collar having a flat wiping surface is preferably placed around the electrodes for securing and holding the electrodes in place when they are scraped by the wiper blade and prevents particulates from depositing between the electrodes. The collar is anchored to the sensor by a recessed screw which also serves as a common electrical ground.

In the preferred embodiment, the flexible blade includes two wiping portions for alternately wiping each electrode and the common ground screw. Each wiping portion is pushed into a bent, flexed posture by the spring mechanism for insuring that the blade's wiping surface when the blade is rotated.

DRAWINGS

The foregoing and other objects, features, and advantages of the invention will be apparent from the following and more particular description of the preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
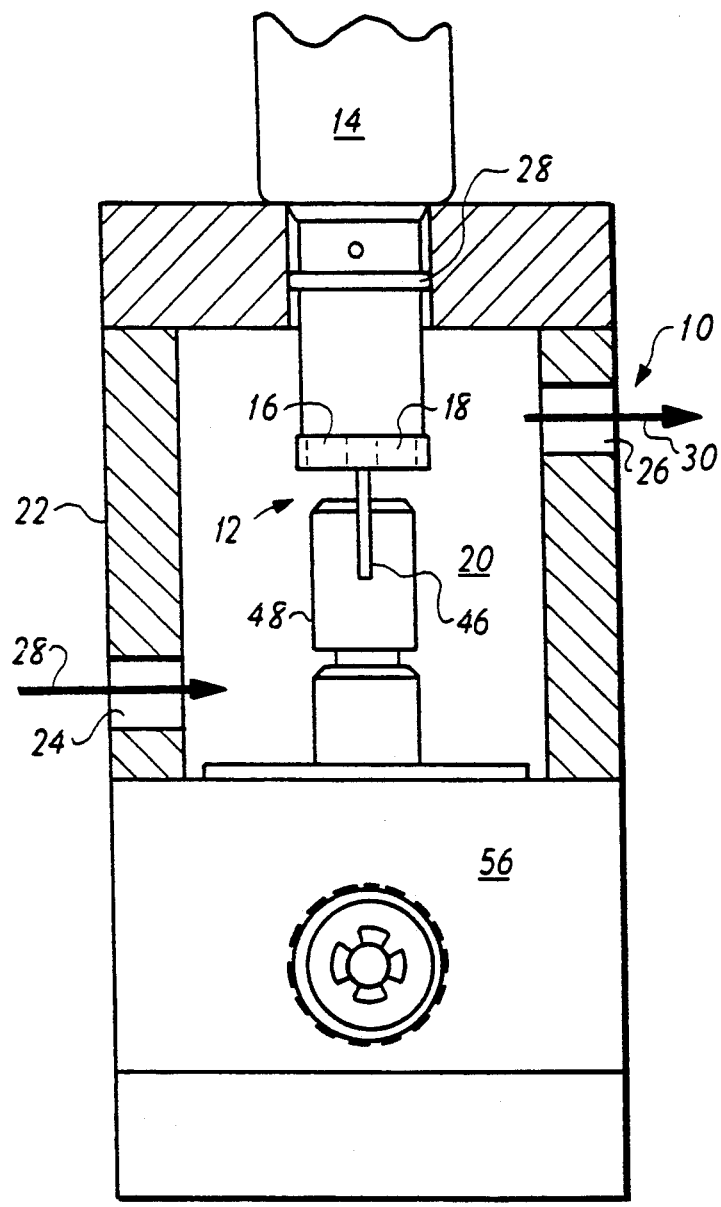
FIG. 1 is a side elevation, partially broken away view of an electrode cleaning system of the present invention.

The electrode cleaning system of the present invention is particularly suited for flow-through or submersible electrochemical sensor assemblies. These assemblies are typically connected in line with a sample line to accommodate external sensor installation. A flow-through electrochemical sensor assembly 10 which includes the electrode cleaning system of the present invention is shown in FIG. 1. Generally, this sensor assembly includes an electrochemical sensor 14 such as The Foxboro Company's 222 and 871 PH and ORP sensor having electrodes 16 and 18 with flat detection surfaces. The sensor 14 is placed in a chamber 20 of a sensor housing 22 to expose the electrodes to process fluid flowing through the chamber 20. An inlet 24 and outlet port 26 allows process fluid into and out of the chamber, as indicated by the arrows 29 and 30, for electrochemical measurement. An O-ring 28 is placed around the neck of the sensor 14 and provides a seal.

Figure 2:
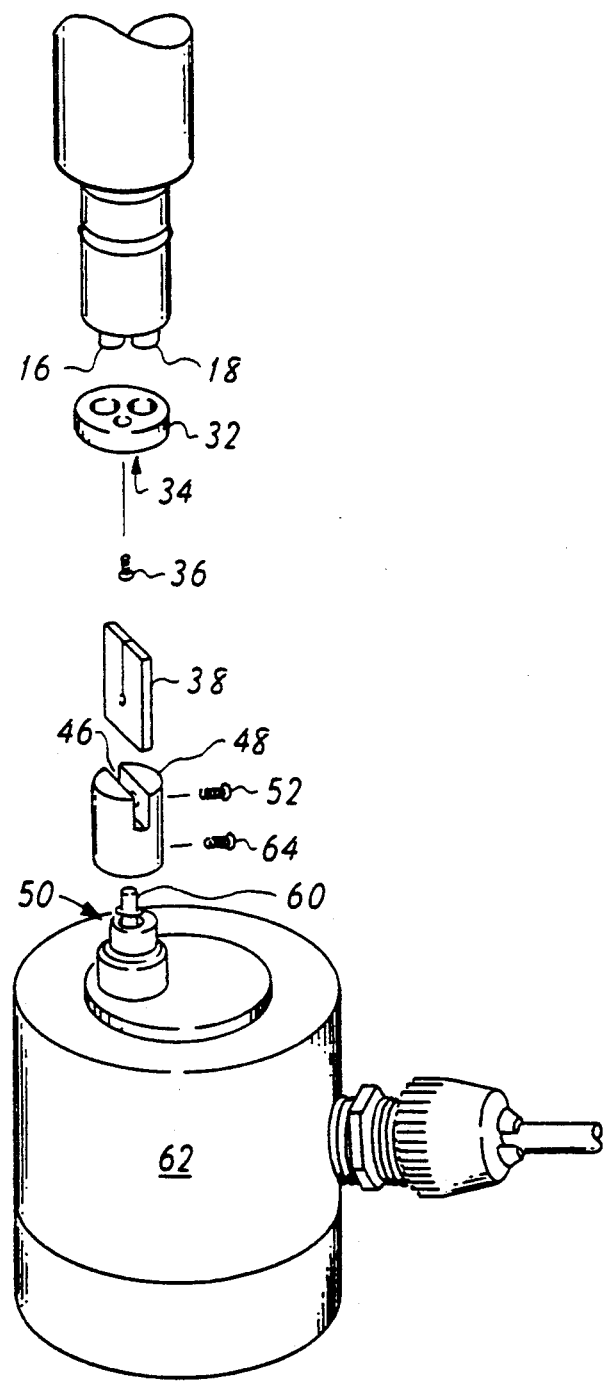
FIG. 2 is an exploded, perspective view of the electrode cleaning system of FIG. 1.

Referring now to FIG. 2, the electrochemical cleaning system of the present invention includes an electrode collar 32 which fits over the electrodes of the sensor. The electrode collar has a flat wiping surface 34 which coincides with the flat wiping surface of the electrodes 16 and 18. The electrode collar 32 is held in place by a holding screw 36, which also serves as a common electrical ground. In the preferred embodiment, the holding screw 36 is recessed in the electrode collar 32 so that its contact surface is flush with the collar's wiping surface 34. The electrode collar 32 is preferably made of PTFE Teflon material but can be made of any chemically resistent, durable plastic or electrically insulating material. Teflon is a trademark of the Du Ponte Company. An advantage of the electrode collar 32 is that it evenly secures the electrodes 16 and 18 and holds them in place when they are scraped cleaned by a rotating wiper blade 38. The collar 32 also prevents any type of buildup between the electrodes 16 and 18 and the grounding screw 36. Together the collar, the electrodes 16 and 18 and the ground screw 36 form a smooth wiping surface with no projected obstructions or restrictive surfaces in the process stream which can accommodate the collection of process matter. In the preferred embodiment, the circumferential edge of the flat wiping surface 34 of the collar 32 is slightly chamfered.

Figure 3:
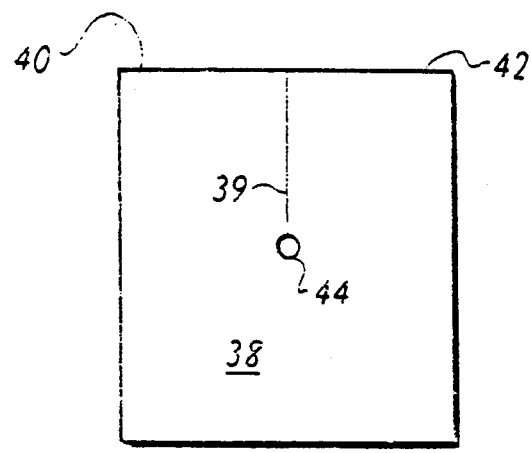
FIG. 3 is an enlarged side elevation view of the wiping blade shown in FIGS. 1 and 2.

The wiper 38 used to scrape the flat wiping surface of the collar 34 and the electrodes 16 and 18 is preferably made of a durable, flexible material such as PTFE Teflon. In the preferred embodiment the wiper 38 has a slit 39 extending approximately half way down the blade thereby separating the blade into two wiping portions 40 and 42 as shown in FIG. 3. When the blade is pressed against the wiping surfaces and rotated, each wiping portion is flexed in opposite directions. A hole 44 is punched at the bottom of the slit to increase the flexibility of the two wiping portions and to prevent the blade from tearing when the wiper scrapes the wiping surfaces.

An advantage of the wiper blade over brushes, as used in the prior art, is that it has a smooth surface and provides low flow resistance. These characteristics assist in keeping the blade clean. Both the movement of the rotating wiper and the stream velocity of the process fluid prevent particulates from accumulating on the smooth wiper blades. Particulates slide off the blade as it rotates and remain in the sample stream. Since the teflon wiper material is thin (approximately 1/16 of an inch in the preferred embodiment) and flexible, it easily scrapes away any sediment bonded to the glass surface of the electrodes or the wiping surface of the collar without damage to either.

Figure 4:
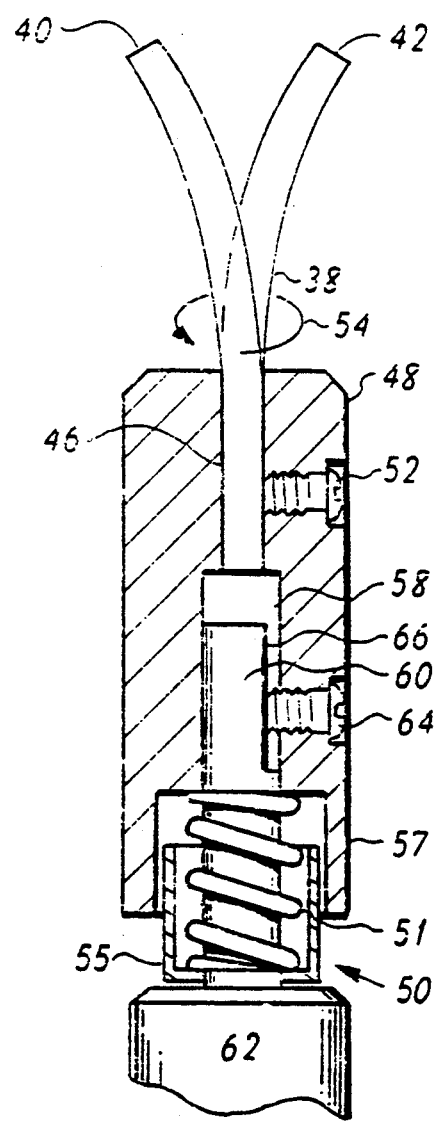
FIG. 4 is an enlarged, partially cross sectional side elevation view of the wiper coupler and a spring mechanism shown in FIGS. 1 and 2.

As shown in FIG. 4, the wiper blade 38 is placed in a slot 46 of a wiper coupler 48 and secured to the wiper coupler 48 by a recessed screw 52. The wiper blade 38 is biased against the wiping surfaces of the electrode collar, electrodes, and ground screw by a spring mechanism 50. The spring mechanism preferably includes a spring 51 having a spring constant which biases the wiper blade 38, as shown in FIG. 1, against the wiping surfaces of the electrodes 16 and 18, ground screw 36 (not shown), and the collar 32. The force of the spring preferably causes each wiping portion 40 and 42 to bend to a flexed position, as shown, when the blade rotates in the direction indicated by arrow 54. The bent posture of the wiping portions insures that they will continuous scrape the wiping surfaces. The spring mechanism further includes a spring shield 55, as shown, having a diameter which allows it to slidably fits within an interior diameter of a skirt portion 57 of the wiper coupler 48. Overlapping portions of the spring shield and the skirt portion help prevent particulates of a process solution from collecting on the spring.

The wiper coupler 48 also includes a passage way 58 for a drive shaft 60 of a motor 62. A recessed locking screw 64 is provided and tightened to come in contact with a flattened portion 66 of the drive shaft 60 to cause the wiper coupler 48 and wiper blade 38 attached thereto to rotate when the motor 62 is activated. The locking screw 64 is not secured too tightly, however, to prevent or limit the biased action of the spring 51 disposed between the wiper coupler 48 and the motor 62. In the preferred embodiment the motor 62 rotates the drive shaft 60 at 1 rpm and thus each electrode is scraped clean once a minute.

While the invention has been particularly shown and described with reference to preferred embodiments thereof, it will be understood by those skilled in the art that various changes in form and details may be made therein without departing from the spirit and scope of the invention, as defined by the appended claims.

We claim:

1. An electrode cleaning system for an electrochemical sensor to remove particulates deposited on electrodes placed in a process fluid, said cleaning system comprising:
   a wiper blade assembly having a flexible blade placed approximate to said electrodes for wiping the electrodes clean; and
   means for rotating the wiper blade assembly about its axis to wipe the electrodes clean of any particulates deposited on the electrode surfaces.

2. The electrode cleaning system of claim 1 wherein said flexible blade includes two wiping portions for alternately wiping each electrode.

3. The electrode cleaning system of claim 1 further comprising a spring means for biasing said wiper blade assembly against the electrodes.

4. The electrode cleaning system of claim 1 wherein said means for rotating includes a motor for continuously rotating said wiper blade assembly about its axis at a rate of one revolution per minute.

5. The electrode cleaning system of claim 1 further including a collar placed around the electrodes to prevent particulates from depositing between the electrodes.

6. The electrode cleaning system of claim 5 wherein said electrodes have a flat detection surface and said collar has a flat wiping surface which is flush with the flat detection surfaces of said electrodes.

7. The electrode cleaning system of claim 5 wherein said collar is fastened to the sensor by a common electrical ground screw placed in contact with the process fluid.

8. The electrode cleaning system of claim 7 wherein said ground screw is recessed within said collar such that a contact surface of the screw is flush with a wiping surface of said collar.

9. An electrode cleaning system for an electrochemical sensor to remove particulates deposited in electrodes placed in a process fluid, said cleaning system comprising:
   a wiper blade assembly placed approximate to said electrodes having a flexible blade for wiping clean the electrodes, wherein said flexible blade includes two wiping sections for alternately wiping each electrode;
   means for rotating the wiper blade assembly about its axis to wipe the electrodes clean of any particulates deposited on the electrode surfaces; and
   spring means for biasing said wiper blade assembly against the electrodes.

10. The electrode cleaning system of claim 9 further including a collar placed around the electrodes to prevent particulates from depositing between the electrodes, said collar having a wiping surface that is flush with wiping surfaces of said electrodes.

11. The electrode cleaning system of claim 10 wherein said collar is anchored to the sensor by a recessed common electrical ground screw having a contact surface that is flush with a wiping surface of said electrodes and said collar.

12. The electrode cleaning system of claim 9 wherein said means for rotating includes a motor for rotating said wiper blade assembly about its axis continuously at a rate of one revolution per minute.

13. An electrode cleaning system for an electrochemical sensor to remove particulates deposited on electrodes placed in a process fluid, said cleaning system comprising:
   a wiper blade assembly placed approximate to said electrodes having a flexible blade for wiping clean the electrodes;
   means for continuously rotating the wiper blade assembly about its axis to simultaneously wipe the electrodes clean of any particulates deposited on the electrode surfaces;
   a spring means for biasing said wiper blade assembly against the electrodes; and
   a collar placed around the electrodes to prevent particulates form depositing between the electrodes.

14. The electrode cleaning system of claim 13 wherein said means for continuously rotating includes a motor for rotating said wiper blade assembly about its axis at a rate of one revolution per minute.

15. The electrode cleaning system of claim 13 further comprising a spring means for biasing said wiper blade assembly against the electrodes.

16. An electrode cleaning system for an electrochemical sensor to remove particulates deposited on electrodes placed in a process fluid, said cleaning system comprising:
   a wiper blade assembly placed approximate to said electrodes having a flexible blade for wiping clean the electrodes, wherein said flexible blade includes two wiping sections, one for alternately wiping each electrode;
   a motor for rotating the wiper blade assembly about its axis to continuously wipe the electrode clean of any particulates deposited on the electrode surfaces, wherein said motor continuously rotates at a rate of one revolution per minute; and
   spring means for biasing said wiper blade assembly against the electrodes; and
   a collar placed around the electrodes to prevent particulates from depositing between the electrodes.

17. The electrode cleaning system of claim 1 wherein said flexible blade is polytetrafluoroethylene.

* * * * *